US00PP32710P2

(12) United States Plant Patent
Beekenkamp

(10) Patent No.: US PP32,710 P2
(45) Date of Patent: Dec. 29, 2020

(54) ***BEGONIA* PLANT NAMED 'BKPBEBVDS'**

(50) Latin Name: *Begonia boliviensis*
Varietal Denomination: BKPBEBVDS

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 16/873,388

(22) Filed: Apr. 4, 2020

(51) Int. Cl.
*A01H 5/02* (2018.01)
*A01H 6/18* (2018.01)

(52) U.S. Cl.
USPC ..... Plt./343

(58) Field of Classification Search
USPC ..... Plt./263.1, 343
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Begonia* plant named 'BKPBEBVDS', characterized by its broadly outwardly spreading to trailing plant habit; freely branching habit; dark green-colored leaves; freely flowering habit; and reddish orange-colored flowers.

2 Drawing Sheets

Figure 1:
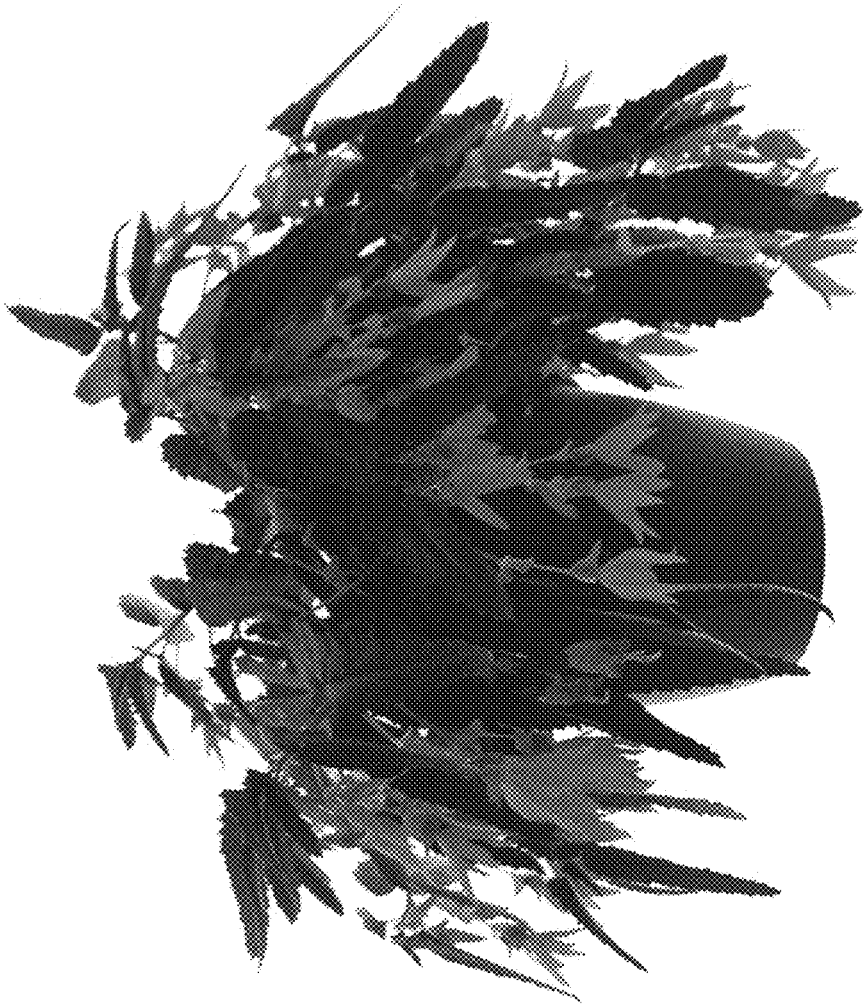

Botanical designation: *Begonia boliviensis*.
Cultivar denomination: 'BKPBEBVDS'.

BACKGROUND OF THE INVENTION

The present invention relates to a new and distinct cultivar of *Begonia* plant, botanically known as *Begonia boliviensis* and hereinafter referred to by the name 'BKPBEBVDS'.

The new *Begonia* plant is a product of a planned breeding program conducted by the Inventor in Maasdijk, The Netherlands. The objective of the breeding program was to develop new freely branching and freely flowering *Begonia* plants with attractive flowers and good garden performance.

The new *Begonia* plant originated from a cross-pollination made by the Inventor in September, 2014 of a proprietary selection of *Begonia boliviensis* identified as code number 11-0026-02, not patented, as the female, or seed, parent with a proprietary selection of *Begonia boliviensis* identified as code number 14-0069-02, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in May, 2015.

Asexual reproduction of the new *Begonia* plant by vegetative tip cuttings in a controlled greenhouse environment in Maasdijk, The Netherlands since December, 2015 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEBVDS'. These characteristics in combination distinguish 'BKPBEBVDS' as a new and distinct *Begonia* plant:

1. Broadly outwardly spreading to trailing plant habit.
2. Freely branching habit.
3. Dark green-colored leaves.
4. Freely flowering habit.
5. Reddish orange-colored flowers.

Plants of the new *Begonia* can be compared to plants of the female parent selection. Plants of the new *Begonia* differ primarily from plants of the female parent selection in the following characteristics:

1. Plants of the new *Begonia* are more compact than plants of the female parent selection.
2. Plants of the new *Begonia* have reddish orange-colored flowers whereas plants of the female parent selection have orange-colored flowers.

Plants of the new *Begonia* can be compared to plants of the male parent selection. Plants of the new *Begonia* differ primarily from plants of the male parent selection in the following characteristics:

1. Plants of the new *Begonia* are more compact than plants of the male parent selection.
2. Plants of the new *Begonia* have reddish orange-colored flowers whereas plants of the male parent selection have dark pink-colored flowers.

Plants of the new *Begonia* can be compared to plants of the *Begonia pendula* X *Begonia boliviensis* 'Encanto Orange', disclosed in U.S. Plant Pat. No. 20,898. In side-by-side comparisons, plants of the new *Begonia* differ from plants of 'Encanto Orange' in the following characteristics:

1. Plants of the new *Begonia* are more compact than plants of 'Encanto Orange'.
2. Plants of the new *Begonia* have reddish orange-colored flowers whereas plants of 'Encanto Orange' have bright orange-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1 of 2) is a side perspective view of a typical flowering plant of 'BKPBEBVDS' grown in a container.

Figure 2:
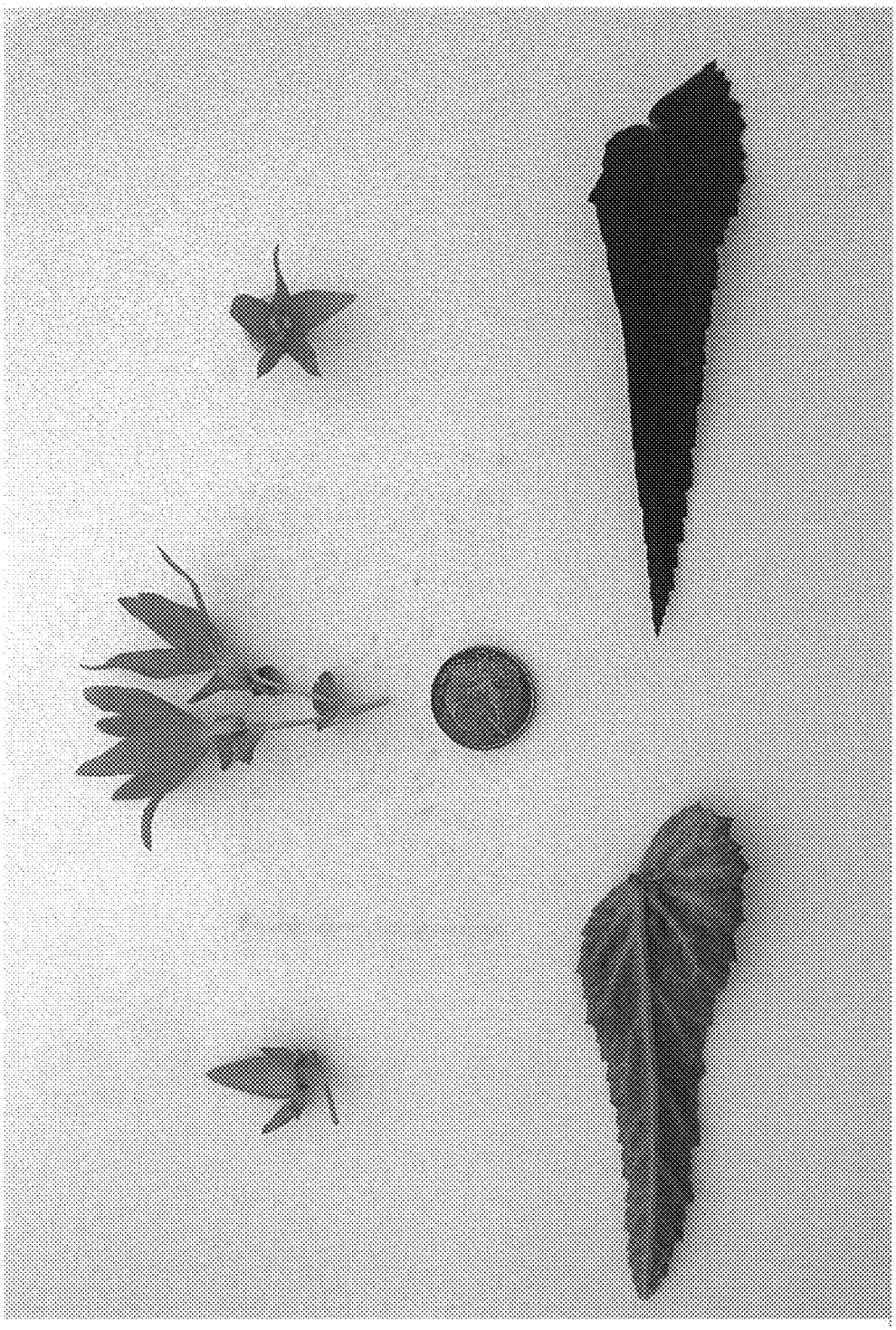

The photograph on the second sheet (FIG. 2 of 2) are close-up views of upper and lower surfaces of typical leaves and flowers of 'BKPBEBVDS'.

DETAILED BOTANICAL DESCRIPTION

Plants used for the aforementioned photographs and following observations and measurements were grown in 10.5-cm containers during the summer in a glass-covered greenhouse in Maasdijk, The Netherlands. During the production of the plants, day temperatures ranged from 19° to 20° C., night temperatures ranged from 18° C. to 19° C. and light levels averaged 6,000 foot-candles. Plants were eleven weeks old when the photographs and the description were taken. In the following description, color references are made to The Royal Horticultural Society Colour Chart, 2015 Edition, except where general terms of ordinary dictionary significance are used.

Botanical classification: *Begonia boliviensis* 'BKPBEBVDS'.

Parentage:

*Female, or seed, parent*.—Proprietary selection of *Begonia boliviensis* identified as code number 11-0026-02, not patented.

*Male, or pollen, parent*.—Proprietary selection of *Begonia boliviensis* identified as code number 14-0069-02, not patented.

Propagation:

*Type*.—By vegetative tip cuttings.

*Time to initiate roots, summer and winter*.—About one week at temperatures about 20° C. to 25° C.

*Time to produce a rooted young plant, summer*.—About 32 days at temperatures about 20° C. to 25° C.

*Time to produce a rooted young plant, winter*.—About 35 days at temperatures about 20° C. to 25° C.

*Root description*.—Fine, fibrous; typically beige in color, actual color of the roots is dependent on substrate composition, water quality, fertilizer type and formulation, substrate temperature and physiological age of roots; plants of the new *Begonia* have not been observed to form tubers.

*Rooting habit*.—Freely branching; dense.

Plant description:

*Plant and growth habit*.—Broadly outwardly spreading and eventually hanging plant habit; plant shape roughly flattened globular; freely branching habit with about three basal branches each with about five lateral branches developing per plant; moderately vigorous growth habit and moderate growth rate.

*Plant height, soil level to top of foliar plane*.—About 13.6 cm.

*Plant height, soil level to top of floral plane*.—About 12.9 cm.

*Plant width*.—About 33.1 cm.

*Lateral branch description*.—Length: About 12.2 cm. Diameter: About 6 mm. Internode length: About 1.5 cm. Strength: Moderately weak, bending with the weight of the leaves and flowers. Aspect: Ranging from about 10° to about 70° from vertical. Texture and luster: Smooth, glabrous; moderately glossy. Color, developing: Close to 165A. Color, fully developed: Close to between 152A and 197A.

*Leaf description*.—Arrangement: Alternate, distichous; simple. Length: About 13.4 cm. Width: About 3.9 cm. Shape: Lanceolate to narrowly ovate. Apex: Acute to broadly and bluntly acute. Base: Oblique; lobes not imbricate. Margin: Serrate; not undulate to slightly undulate. Texture and luster, upper and lower surfaces: Smooth, glabrous; slightly velvety; slightly glossy. Venation pattern: Pinnate. Color: Developing leaves, upper surface: Close to between 146A and 147A. Developing leaves, lower surface: Close to 178A and 183A. Fully expanded leaves, upper surface: Close to between NN137A and 147A; venation, close to 143A to 143B. Fully expanded leaves, lower surface: Close to 148B tinged with close to 183C to 183D; venation, close to 146C. Petioles: Length: About 1.5 cm. Diameter: About 3 mm. Texture and luster, upper and lower surfaces: Smooth, glabrous; moderately glossy. Strength: Low. Color, upper surface: Close to 152A. Color, lower surface: Close to 152A to 152B. Stipules: Quantity per leaf: Two. Length: About 5 mm. Width: About 3 mm. Shape: Ovate. Apex: Acute. Base: Broadly cuneate. Margins: Entire, finely ciliate. Color, upper and lower surfaces: Close to 146D; venation, close to 177C to 177D.

Flower description:

*Flowering habit*.—Rotate single male and female flowers; flowers arranged in axillary cymes; freely flowering habit with about three flowers per cyme and about 250 flowers developing per plant during the flowering season; flowers nodding or drooping.

*Fragrance*.—None detected.

*Natural flowering season*.—Long flowering period; plants flower freely and continuously from spring into the autumn in The Netherlands.

*Flower longevity*.—Individual flowers last about ten days on the plant; flowers not persistent.

*Inflorescence height* (*including peduncle*).—About 8.5 cm.

*Inflorescence diameter*.—About 5.1 cm.

*Flower buds*.—Length: About 2 cm to 2.3 cm. Diameter: About 4 mm to 9 mm. Shape: Ovate; flattened. Texture and luster: Smooth, glabrous; velvety; matte. Color: Close to 41B.

*Male flowers*.—Size: About 6 mm by 3 cm. Tepals: Quantity per flower and arrangement: Four in two whorls. Length, outer tepals: About 3 cm. Length, inner tepals: About 2.7 cm. Width, outer tepals: About 1.3 cm. Width, inner tepals: About 5 mm. Shape, outer tepals: Ovate. Shape, inner tepals: Oblanceolate. Apex, outer tepals: Acute. Apex, inner tepals: Bluntly acute. Base, outer and inner tepals: Cuneate. Margin, outer and inner tepals: Entire; not undulate. Texture and luster, outer and inner tepals, upper surface: Smooth, glabrous; velvety; matte. Texture and luster, outer and inner tepals, lower surface: Smooth, glabrous; velvety; matte and towards the base, slightly glossy. Color, outer and inner tepals: When opening, upper surface: Close to 40C. When opening, lower surface: Close to between 41B and 41C. Fully opened, upper surface: Close to 40B; towards the apex, close to 41C; venation, close to 40B and towards the apex, close to 41C; color does not change with development. Fully opened, lower surface: Close to 40C; towards the apex, close to 41B; venation, close to 40C and towards the apex, close to 41B; color does not change with development. Tepaloids: None observed on male flowers.

*Female flowers*.—Size: About 3.2 cm by 3.5 cm. Tepals: Quantity per flower and arrangement: Five in two whorls; outer whorl with two tepals and inner whorl with three tepals. Length, outer tepals: About 3 cm. Length, inner tepals: About 2.8 cm. Width, outer tepals: About 1 cm. Width, inner tepals: About 5.5 mm. Shape, outer tepals: Narrowly ovate. Shape, inner tepals: Oblanceolate. Apex, outer tepals: Acute. Apex, inner tepals: Bluntly acute. Base, outer and inner tepals: Cuneate. Margin, outer and inner tepals: Entire; not undulate. Texture and luster, outer and inner tepals, upper and lower surfaces: Smooth, glabrous; velvety; matte. Color, outer and inner tepals: When opening, upper and lower surfaces: Close to 40C. Fully opened, upper surface: Close to 40C; venation, close to 40C; color does not change with development. Fully opened, lower surface: Close to 40C; towards the apex, close to between 41B and 41C; venation, close to 40C and towards the apex, close to between 41B and 41C; color does not change with development. Tepaloids: None observed on female flowers.

*Peduncles*.—Length: About 3.2 cm. Diameter: About 1.5 mm. Angle: About 45° from lateral branch axis. Strength: Moderately weak; flexible and bending with the weight of the flowers. Texture and luster: Smooth, glabrous; moderately glossy. Color: Close to between 146C and 152C; upper surface tinged with close to 171A.

*Pedicels, male and female flowers*.—Length, male flowers: About 1.1 cm. Length, female flowers: About 2.5 cm. Diameter: About 1.25 mm. Angle: About 25° from the peduncle axis. Strength: Moderately weak; flexible, bending with the weight of the flowers. Texture and luster: Smooth, glabrous; glossy. Color: Close to 144B moderately tinged with close to 173B; upper surface tinged with close to 173B.

*Flower bracts*.—Quantity per flower and arrangement: Two, at the top of the peduncles. Length: About 1.1 cm. Width: About 1.4 cm. Shape: Roughly reniform. Apex: Rounded. Base: Broadly cuneate. Margin: Finely ciliate. Texture and luster, upper and lower surfaces: Smooth, glabrous; slightly glossy. Color, upper and lower surfaces: Close to 145A to 145C; towards the margins and apex, close to 39A.

*Reproductive organs*.—Androecium: Present only on male flowers. Stamen quantity per flower: About five. Filament length: About 2.5 mm. Filament color: Close to 20C. Anther size: About 1 mm by 1 mm. Anther shape: Obovate. Anther color: Close to 21A to 21B. Amount of pollen: Scarce. Pollen color: Close to 4D. Gynoecium: Present only on female flowers. Quantity per flower: Three. Pistil length: About 1.1 cm. Stigma diameter: About 4 mm. Stigma shape: Cleft. Stigma color: Close to 21A. Style length: About 1 cm. Style color: Close to 25C. Ovary color: Close to 145B and apex, close to 45C. Seeds and fruits: To date, seed and fruit development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BKPBEBVDS' as illustrated and described.

* * * * *